(12) United States Patent
Kwon

(10) Patent No.: US 11,607,313 B2
(45) Date of Patent: Mar. 21, 2023

(54) IMPLANT DEVICE FOR PROMOTING BONE GROWTH

(71) Applicant: IKEY CO., LTD, Busan (KR)

(72) Inventor: Yong Won Kwon, Busan (KR)

(73) Assignee: IKEY CO., LTD, Busan (KR)

( * ) Notice: Subject to any disclaimer, the term of this patent is extended or adjusted under 35 U.S.C. 154(b) by 0 days.

(21) Appl. No.: 17/013,133

(22) Filed: Sep. 4, 2020

(65) Prior Publication Data
US 2020/0397585 A1  Dec. 24, 2020

Related U.S. Application Data

(62) Division of application No. 15/779,437, filed as application No. PCT/KR2016/012050 on Oct. 26, 2016, now abandoned.

(30) Foreign Application Priority Data

Dec. 14, 2015 (KR) .......................... 10-2015-0177956

(51) Int. Cl.
*A61F 2/28* (2006.01)
*A61B 17/56* (2006.01)
(Continued)

(52) U.S. Cl.
CPC ............... *A61F 2/28* (2013.01); *A61B 17/56* (2013.01); *A61B 17/68* (2013.01);
(Continued)

(58) Field of Classification Search
CPC .................. A61F 2/28; A61F 2/30749; A61F 2002/30092; A61F 2002/3055;
(Continued)

(56) References Cited

U.S. PATENT DOCUMENTS

| 5,449,359 A | 9/1995 | Groiso |
| 7,063,706 B2 * | 6/2006 | Wittenstein ........ A61B 17/7216 606/90 |

(Continued)

FOREIGN PATENT DOCUMENTS

| JP | 2007-519478 A | 7/2007 |
| KR | 10-2009-0081173 A | 7/2009 |

(Continued)

*Primary Examiner* — Christopher D. Prone
(74) *Attorney, Agent, or Firm* — Bridgeway IP Law Group, PLLC; Sang Ho Lee; Hyun Woo Shin

(57) ABSTRACT

In order to promote bone growth without damage of a growth plate to improve the stability of a procedure, provided is an implant device for promoting bone growth, the device including: a first implant bar implanted to penetrate a metaphysis corresponding to the inside of a growth plate of a long bone to be treated; a second implant bar implanted to penetrate an epiphysis of the outside of the growth plate; and a stimulation elongation means disposed close to the external surface of the long bone to be treated and installed under skin tissues surrounding the long bone to be treated, and being elongated between end portions of the implant bars to increase a gap between the implant bars to cause the growth plate to be extended.

4 Claims, 5 Drawing Sheets

(51) Int. Cl.
*A61B 17/68* (2006.01)
*A61F 2/30* (2006.01)

(52) U.S. Cl.
CPC ........ *A61F 2/30771* (2013.01); *A61B 17/683* (2013.01); *A61B 2017/681* (2013.01); *A61F 2/30749* (2013.01); *A61F 2002/3055* (2013.01); *A61F 2002/30092* (2013.01); *A61F 2002/3093* (2013.01); *A61F 2002/30904* (2013.01)

(58) Field of Classification Search
CPC ... A61F 2002/30904; A61F 2002/3093; A61B 17/064; A61B 17/88; A61B 17/56; A61B 17/68
See application file for complete search history.

(56) References Cited

U.S. PATENT DOCUMENTS

| | | | |
|---|---|---|---|
| 2003/0139746 | A1 | 7/2003 | Groiso |
| 2010/0036430 | A1 | 2/2010 | Hartdegen et al. |
| 2011/0196371 | A1* | 8/2011 | Forsell ............... A61B 17/7216 606/62 |
| 2012/0209338 | A1 | 8/2012 | Groiso |

FOREIGN PATENT DOCUMENTS

| | | |
|---|---|---|
| KR | 10-2013-0108366 A | 10/2013 |
| KR | 10-1666527 B1 | 10/2016 |

\* cited by examiner

IMPLANT DEVICE FOR PROMOTING BONE GROWTH

CROSS-REFERENCE TO RELATED APPLICATIONS

This application is divisional application of U.S. application Ser. No. 15/779,437 filed on May 25, 2018, which is a national-stage application under 35 USC § 371 of international application No. PCT/KR2016/012050 filed on Oct. 26, 2016, and claims priority under 35 USC § 119 to the Korean patent application No. 10-2015-0177956 filed on Dec. 14, 2015, the entire disclosures of which are incorporated herein by reference in their entirety.

TECHNICAL FIELD

The present disclosure relates to an implant device for promoting bone growth, and more particularly, to an implant device for promoting bone growth, which is configured to promote bone growth without damage of a growth plate, thereby improving the safety of a procedure.

BACKGROUND ART

In general, a long bone, such as a femur, a tibia, a humerus, and the like, includes a diaphysis forming a central portion of the long bone, a metaphysis provided at both end portions of the diaphysis, and an epiphysis provided outside the metaphysis. Also, a growth plate is located between the metaphysis and the epiphysis. In this case, a medullary cavity, which is filled with bone marrow, is present inside the diaphysis, and a bone may be grown by the growth plate.

Here, it is known that a length growth of the growth plate of the long bone is inhibited when the growth plate of the long bone receives compressive force inward from the epiphysis toward the metaphysis, while the length growth of the growth plate of the long bone is promoted when the growth plate of the long bone receives tensile stress outward from the metaphysis toward the epiphysis.

Thus, conventionally, a device configured to promote bone growth by applying an outward tensile stress to a growth plate has been devised.

However, the device according to the related art configured to promote bone growth is installed outside the human body and configured to apply tensile stress. Since skin tissues are subject to pressure together during the stimulation of the growth plate, excessive force applied to the skin tissues, thereby causing a wearer to suffer pain. In addition, there has been a problem that the wearer cannot live everyday life due to a device exposed outside.

Furthermore, since it is hard to apply uniform tensile stress to each portion of the growth plate, there have been serious problems of causing non-uniform bone growth or damaging the growth plate by applying excessive force to the growth plate.

DESCRIPTION OF EMBODIMENTS

Technical Problem

In order to solve the above-described problems, there is provided an implant device for promoting bone growth, which is configured to promote bone growth without damage of a growth plate, thereby improving the safety of a procedure.

Solution to Problem

According to an aspect of the present disclosure, the present disclosure provides an implant device for promoting bone growth, the implant device including: a first implant bar implanted to penetrate a metaphysis corresponding to the inside of a growth plate of a long bone to be treated; a second implant bar implanted to penetrate an epiphysis of the outside of the growth plate; and a stimulation elongation unit located close to an external surface of the long bone to be treated and installed in skin tissues surrounding the long bone to be treated, wherein the stimulation elongation unit is elongated between end portions of the respective implant bars to increase a distance between the first implant bar and the second implant bar so that the growth plate may be extended.

Advantageous Effects of Disclosure

By using the above-described solutions, an implant device for promoting bone growth according to the present disclosure provides the following effects.

First, implant bars implanted to penetrate both sides of a growth plate of a long bone stimulate the growth plate with the elongation of a stimulation elongation unit, and each component may be mounted in a compact structure in skin tissues. Thus, a wearer can live everyday life with the implant device worn, so that a convenience of using a product can be improved.

Second, the stimulation elongation unit is connected to both exposed ends of each of a first implant bar and a second implant bar that are implanted to penetrate inner and outer sides of the growth plate to thereby elongate the both exposed ends of each of the first and second implant bars. Thus, the elongation of a central portion and an outer portion of the growth plate portion can be uniformly promoted at the same time.

Third, a variation of an elongation rod portion located in a direction in which the long bone is curved is set to be larger than a variation of an elongation rod portion located on another side so that rotational deformation may be induced. Accordingly, a more active growth promotion effect may be given to the growth plate corresponding to the direction in which the long bone is curved than to the growth plate corresponding to a direction opposite to the direction in which the long bone is curved. Thus, the curved long bone may be corrected.

Fourth, when the stimulation elongation unit compactly includes a single arc-shaped member including a shape memory alloy material of which a curvature is reduced by body temperature, a sensation of foreign materials can be minimized in skin tissues. Also, the stimulation elongation unit is elastically deformed into a round shape and pressure is dispersed slantwise in an arc direction during the shape deformation. Thus, by giving stable stimulation, damage of the growth plate can be prevented to improve safety of a product.

BEST MODE

The best mode for embodying the present disclosure will be described in further detail below with reference to the accompanying drawings.

Mode of Disclosure

Hereinafter, an implant device for promoting bone growth according to exemplary embodiments of the present disclosure will be described in detail with reference to the accompanying drawings in which the exemplary embodiments are shown.

Figure 1:
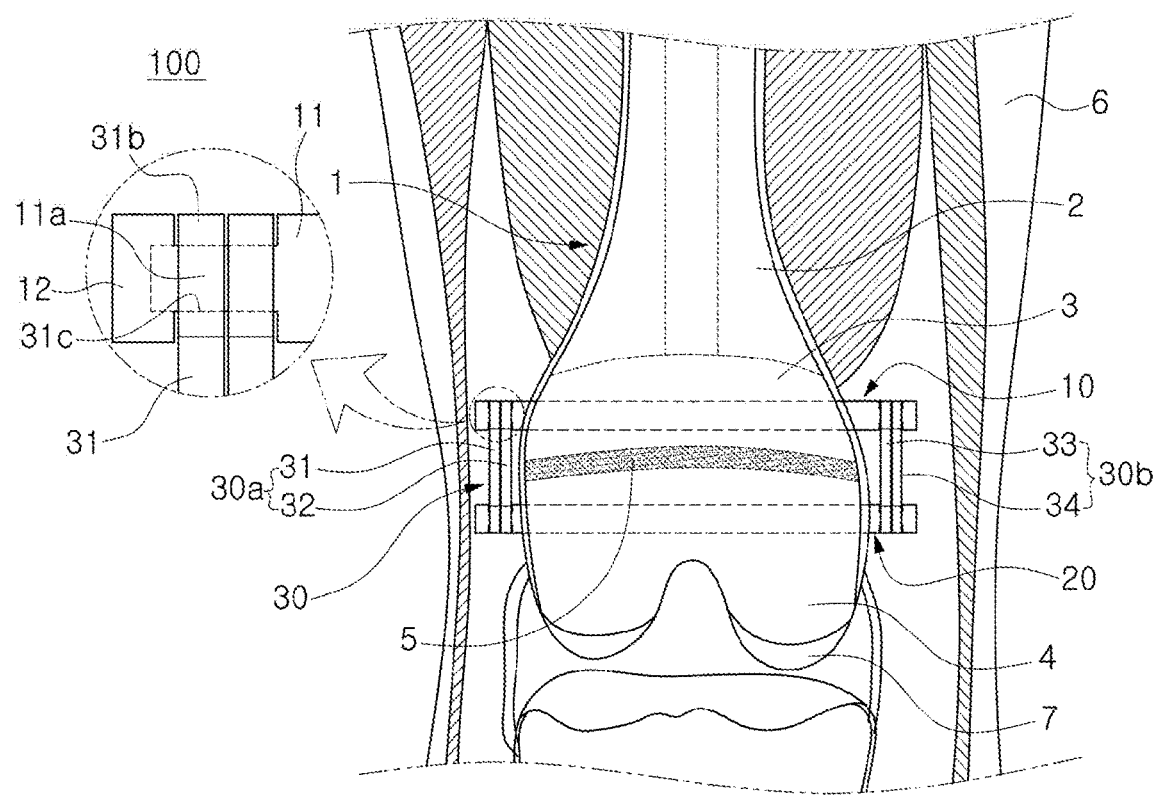
FIG. 1 is a front view of an implant device for promoting bone growth according to a first embodiment of the present disclosure.
Figure 2:
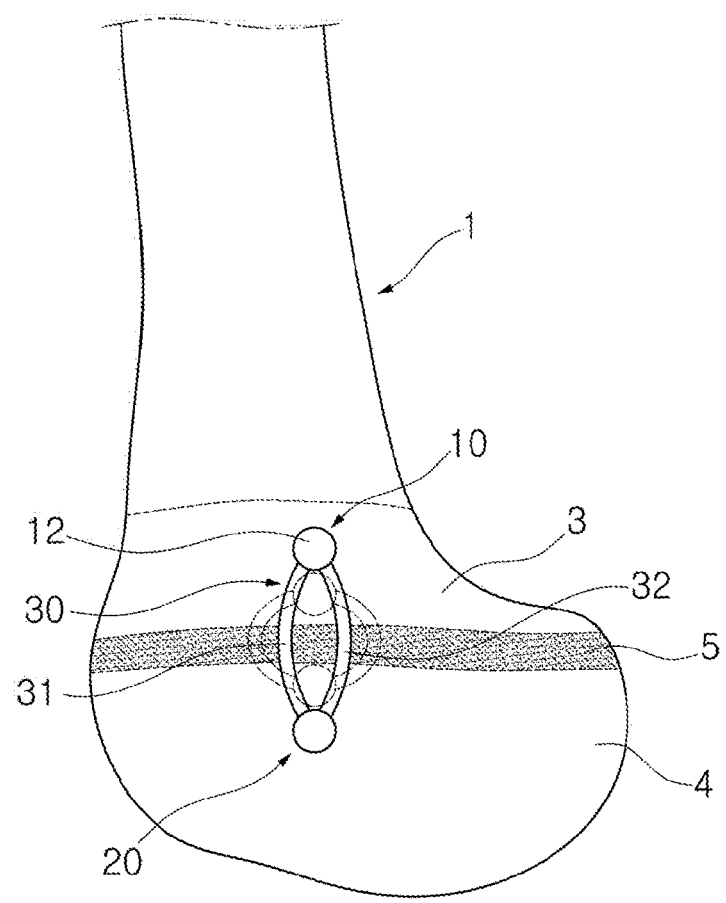
FIG. 2 is a side view of the implant device for promoting bone growth according to the first embodiment of the present disclosure.
Figure 3:
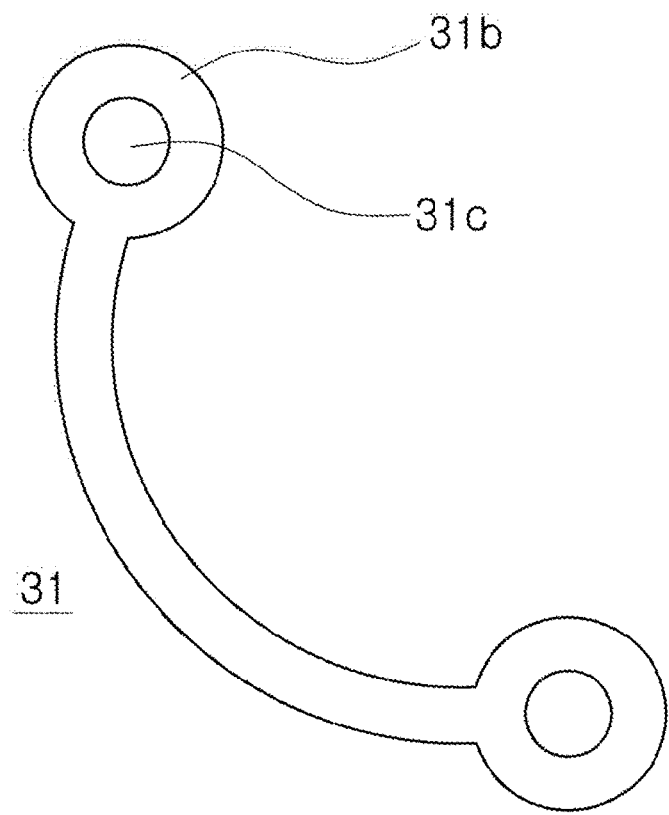
FIG. 3 is a diagram of an example of a stimulation elongation unit of the implant device for promoting bone growth according to the first embodiment of the present disclosure.

FIG. 1 is a front view of an implant device for promoting bone growth according to a first embodiment of the present disclosure. FIG. 2 is a side view of the implant device for promoting bone growth according to the first embodiment of the present disclosure. FIG. 3 is a diagram of an example of a stimulation elongation unit of the implant device for promoting bone growth according to the first embodiment of the present disclosure.

As shown in FIGS. 1 to 3, an implant device 100 for promoting bone growth includes a first implant bar 10, a second implant bar 20, and a stimulation elongation unit 30.

Here, the implant device 100 for promoting bone growth refers to a device configured to promote the growth of a length of a bone by applying tensile stress to a peripheral portion of a growth plate 5 so that the growth plate 5 may be pulled up and down.

Meanwhile, the first implant bar 10 is implanted to penetrate a metaphysis 3 corresponding to the inside of the growth plate 5 of a long bone 1 to be treated, and the second implant bar 20 is located parallel to the first implant bar 10 and implanted to penetrate an epiphysis 4 of the outside of the growth plate 5.

In this case, the long bone 1 to be treated refers to a portion of a long bone (e.g., a femur, tibia, a humerus, and the like) for which a procedure for growth promotion is planned. The long bone 1 to be treated may be set by a judgement of a practitioner or a request of a person to be treated.

Here, the long bone 1 includes a diaphysis 2, the metaphysis 3, the growth plate 5, the epiphysis 4, an articular cartilage 7, and the like, and the first implant bar 10 and the second implant bar 20 are preferably implanted in the metaphysis 3 and the epiphysis 4, respectively, which are located on both sides of the growth plate 5.

Meanwhile, directions in which the first implant bar 10 and the second implant bar 20 are located are set to correspond to a target growth direction of the long bone 1. Also, the first implant bar 10 and the second implant bar 20 are implanted parallel to each other in a direction perpendicular to the target growth direction of the long bone 1. Thus, when the first implant bar 10 and the second implant bar 20 are spaced apart from each other, uniform tensile stress may be applied to each portion of the growth plate 5.

In addition, the first implant bar 10 and the second implant bar 20 preferably include a titanium-based alloy or a Teflon-based synthetic resin, which does not cause a rejection reaction to the human body.

Specifically, when the long bone 1 to be treated is set, skin tissues 6 corresponding to the long bone 1 are incised to expose the metaphysis 3 and the epiphysis 4, and a treatment hole is formed in the metaphysis 3 and the epiphysis 4 using a drill device.

In this case, the first implant bar 10 and the second implant bar 20 are implanted in the metaphysis 3 or the epiphysis 4 through the formed treatment hole. Here, the first implant bar 10 and the second implant bar 20 are provided to have lengths greater than lateral thicknesses of implanted portions, so that both end portions of the first implant bar 10 and the second implant bar 20 are exposed to both side portions of the long bone 1.

Naturally, the first implant bar 10 and the second implant bar 20 may be provided to have the same length or provided to have respectively different lengths.

Here, the stimulation elongation unit 30 is coupled to the both exposed end portions of each of the implant bars 10 and 20. Each of the implant bars 10 and 20 is applied with pressure due to the elongation of the stimulation elongation unit 30 so that the implant bars 10 and 20 may be spaced apart from each other. Thus, tensile stress capable of promoting length growth of the long bone 1 may be applied to the growth plate 5.

In this case, the first implant bar 10 and the second implant bar 20 may have a hexagonal pillar shape or a cylindrical shape, so that warpage of the first implant bar 10 and the second implant bar 20 may be prevented when pressure is applied by the stimulation elongation unit 30. Also, pressure applied to each of the implant bars 10 and 20 may be dispersed into the treatment hole so that damage of the treatment hole and the epiphysis/metaphysis may be prevented.

Meanwhile, the stimulation elongation unit 30 is located close to an external surface of the long bone 1 to be treated, and installed in the skin tissues 6 surrounding the long bone 1 to be treated. Also, the stimulation elongation unit 30 is elongated between the end portions of each of the implant bars 10 and 20 to increase a distance between the implant bars 10 and 20 so that the growth plate 5 may be extended.

In this case, a pair of stimulation elongation units 30 are more preferably provided between one end portions of the implant bars 10 and 20 and between another end portions of the implant bars 10 and 20, respectively. Also, the respective stimulation elongation units 30 may be formed to be elongated by the same length or formed to be elongated by different lengths.

Specifically, the stimulation elongation unit 30 preferably includes a first elongation rod portion 30a located between one end portion of the first implant bar 10 and one end portion of the second implant bar 20, which are exposed to one side portion of the long bone 1. Also, the stimulation elongation unit 30 preferably includes a second elongation rod portion 30b located between another end portion of the first implant bar 10 and another end portion of the second implant bar 20, which are exposed to another side portion of the long bone 1.

In this case, the stimulation elongation unit 30 may be coupled to each of the implant bars 10 and 20 so that the implant bars 10 and 20 may be connected to each other along a surface of the long bone 1. Also, after the stimulation elongation unit 30 is coupled to each of the implant bars 10 and 20, the incised skin tissues 6 are sutured to expose the long bone 1, and the implant device 100 for promoting bone growth may be installed between the long bone 1 and the skin tissues 6.

As described above, with the elongation of the stimulation elongation unit 30, the growth plate 5 may be stimulated by the respective implant bars 10 and 20 that are implanted to penetrate both sides of the growth plate 5 of the long bone 1. In this case, each of components, such as each of the implant bars 10 and 20, the stimulation elongation unit 30, and the like, may be mounted in a compact structure in the skin tissues.

Accordingly, after the device is installed in the long bone 1 to be treated, only if the skin tissues 6 are healed, a wearer may live everyday life with the device worn, so that a convenience of using a product may be improved.

Here, the stimulation elongation unit 30 is elongated to increase a distance between the implant bars 10 and 20 so that the growth plate 5 may be extended.

Specifically, the growth plate 5 consists of a population of chondrocytes. In this case, the growth plate 5 may continuously generate new bone marrow through processes, such as proliferation of chondrocytes, hypertrophy, secretion of extracellular matrices, invasion of blood vessels and osteoprogenitor cells, ossification, and the like In this case, it is preferably understood that when the growth plate 5 is extended, the growth plate 5 is pulled in a direction in which a space between the metaphysis 3 and the epiphysis 4 widens. Furthermore, with an increase in distance between the metaphysis 3 and the epiphysis 4, a process of growing the length of the long bone 1 using the growth plate 5 may be promoted.

Here, since there is a possibility that the chondrocytes will be damaged by even an impact of jumping on a hard floor, tensile stress applied to each of the implant bars 10 and 20 by the stimulation elongation unit 30 is preferably set to a pressure equal to or less than a pressure under which the chondrocytes may be broken.

In this case, the stimulation elongation unit 30 includes a pair of elongation rod portions 30a and 30b so that both end portions of each of the implant bars 10 and 20 may be applied with pressure at the same time. Therefore, uniform stimulation may be applied to each portion of the growth plate 5. As a result, abnormal growth of the long bone 1 due to non-uniform stimulation may be prevented, and the long bone 1 may be accurately grown to correspond to a planned growth direction.

As described above, the stimulation elongation unit 30 may be elongated to increase a distance between the implant bars 10 and 20 installed on both sides of the growth plate 5. Thus, tensile stress pulling outward may be applied to the growth plate 5, and the growth of a length of the long bone 1 may be promoted.

In addition, without simultaneously pulling the skin tissues 6 and the long bone 1 as in the related art, components (e.g., the implant bars 10 and 20, and the stimulation elongation unit 30, and the like) are directly installed at a long bone in the skin tissues 6. Thus, smooth stimulation may be given to the growth plate 5 without damage of the skin tissues 6, thereby improving growth promotion performance of a product.

Meanwhile, it is preferable that both end portions of the stimulation elongation unit 30, that is, both end portions of each of the elongation rod portions 30a and 30b are coupled to the end portions of the first implant bar 10 and the second implant bar 20.

That is, an upper end portion of the first elongation rod portion 30a is preferably coupled to one end portion of the first implant bar 10, while a lower end portion of the first elongation rod portion 30a is preferably coupled to one end portion of the second implant bar 20. Also, an upper end portion of the second elongation rod portion 30b is preferably coupled to the first implant bar 10, while a lower end portion of the second elongation rod portion 30b is coupled to another end portion of the second implant bar 20.

In this case, each of the elongation rod portions 30a and 30b preferably includes a round bar shape including an elastic shape memory alloy material, which is transformed to reduce a curvature of each of the elongation rod portions 30a and 30b at a predetermined first temperature or higher.

That is, each of the elongation rod portions 30a and 30b includes an arc-shaped round bar and includes a shape memory alloy, which has a large curvature below the predetermined first temperature and has a reduced curvature at the predetermined first temperature or higher.

In this case, when a shape has a large curvature, it is understood that the shape has a large curved extent. When a shape has a reduced curvature, it is understood that the shape has a reduced curved extent and becomes close to a straight shape.

Specifically, the shape memory alloy refers to an alloy having a property of returning to a defined shape at a predetermined constant temperature. Here, the shape memory alloy may include various kinds of alloys, such as a nickel (Ni)/titanium (Ti) alloy, a copper/zinc alloy, a gold/copper/zinc alloy, and the like. The shape memory ally preferably includes a nitinol (Ni—Ti) alloy, which minimizes a negative reaction of the human body.

In this case, each of the elongation rod portions 30a and 30b may include a 1-way shape memory alloy so that an alloy configured to memorize an arbitrary shape is put into a Martensite phase by a cooling process to change a shape, and returns to the memorized shape by a heating process. Moreover, each of the elongation rod portions 30a and 30b may include a two-way shape memory alloy configured to memorize both an Austenite-phase shape and a Martensite-phase shape so that a shape of each of the elongation rod portions 30a and 30b may be shifted by heating and cooling processes.

For example, when each of the elongation rod portions 30a and 30b includes a one-way shape memory alloy, a shape into which each of the elongation rod portions 30a and 30b is to be deformed may be set to a bar shape that is close to a straight line having a small curvature, and the first temperature may be set at about 36.5° C., which is a normal body temperature.

In this case, each of the elongation rod portions 30a and 30b is deformed into a bar shape, which is close to a circular shape having a large curvature, below the first temperature and then installed in the body. Each of the elongation rod portions 30a and 30b is heated to the first temperature or higher by body temperature and gradually transformed to correspond to a memorized shape, and has a reduced curvature.

Naturally, each of the elongation rod portions 30a and 30b may include a two-way shape memory alloy. Each of the elongation rod portions 30a and 30b may store a bar shape close to a circular shape having a large curvature below the first temperature, and store a bar shape close to a straight line having a small curvature at the first temperature or higher.

In this case, after each of the elongation rod portions 30a and 30b is installed in the body in a cooled state, each of the elongation rod portions 30a and 30b is heated to reduce a curvature of each of the elongation rod portions 30a and 30b. Thus, a distance between the first implant bar 10 and the second implant bar 20 may increase.

Here, the elongation rod portions 30a and 30b connect the end portions of each of the implant bars 10 and 20 and are slantwise formed forward or backward so that the elongation rod portions 30a and 30b may be closely adhered to the surface of the long bone 1. Also, each of the elongation rod portions 30a and 30b may be coupled to the end portions of the first implant bar 10 and the second implant bar (20) in an inclined direction.

In this case, when the curvature of each of the elongation rod portions 30a and 30b is reduced, the end portions of the implant bars 10 and 20 are applied slantwise with pressure in arc directions of the elongation rod portions 30a and 30b.

That is, a pressure due to shape deformation of the elongation rod portions 30a and 30b may not be directly applied in a direction in which the implant bars 10 and 20 are spaced apart from each other but be dispersed slantwise in the arc directions.

Furthermore, the arc-shaped elongation rod portions 30a and 30b may be elastically deformed due to round shapes thereof. Therefore, the arc-shaped elongation rod portions 30a and 30b may absorb compressive force applied to each of the implant bars 10 and 20 and stably stimulate the implant bars 10 and 20.

As described above, the stimulation elongation unit 30 is provided in a round shape and deformed elastically. Pressure generated during the deformation of the stimulation elongation unit 30 is dispersed slantwise in an arc direction and applied to each of the implant bars 10 and 20. Thus, stimulation may be stably given without damage of the growth plate 5 or the long bone 1, which may be caused due to an excessive pressure load, and thus the safety of a product may be enhanced.

Furthermore, the elongation rod portions 30a and 30b include a single arc-shaped member, which is formed of a shape memory alloy to increase a distance between the implant bars 10 and 20 so that a curvature of the single arc-shaped member may be reduced by body temperature. Thus, since a simplified structure facilitates miniaturization of the device, a sensation of foreign materials may be minimized in the skin tissues 6.

Meanwhile, each of the elongation rod portions 30a and 30b includes a pair of elongation rod portions, which are located in arc shapes to be symmetric to each other. Ring binding portions 31b are preferably hinge-coupled to both end portions of each of the elongation rod portions 30a and 30b and surround narrow tubular portions 11a formed at the end portions of the implant bars 10 and 20.

That is, the first elongation rod portion 30a includes one elongation rod portion 31 formed slantwise backward and another elongation rod portion 32 formed slantwise forward. The second elongation rod portion 30b also includes a pair of elongation rod portions 33 and 34 formed slantwise forward and backward, respectively.

In this case, a force generated by the first elongation rod portion 31 formed slantwise backward and a force generated by the first elongation rod portion 32 formed slantwise forward are generated in opposite inclined directions. Here, due to interaction of the two forces, the forces generated in forward and backward directions, which are conflicting directions, counterbalance each other and are removed, and only a force generated in a vertical direction corresponding to a direction in which the implant bars 10 and 20 are located remains.

Thus, directions of forces generated by the first elongation rod portion 31 and 32 and the second elongation rod portion 33 and 34 may be uniformized, so that distortion and deformation due to forward/backward differences in forces applied to both end portions of the implant bars 10 and 20 may be prevented. Furthermore, force may be applied to the both end portions of the implant bars 10 and 20 in a uniform thickness so that the growth plate 5 may be stably stimulated.

Meanwhile, each of the elongation rod portions 30a and 30b is preferably coupled to the end portions of each of the implant bars 10 and 20 through the ring binding portions 31b formed at both end portions of each of the elongation rod portions 30a and 30b.

Specifically, each of the implant bars 10 and 20 preferably includes a base bar 11 including narrow tubular portions 11a provided at both end portions thereof and fastening portions 12 coupled to end portions of the narrow tubular portions 11a.

In this case, binding holes 31c are formed inside the ring binding portions 31b. Here, in a state in which the narrow tubular portions 11a penetrate the ring binding portions 31b through the binding holes 31c, the fastening portions 12 may be coupled to the end portions of the narrow tubular portions 11a so that the elongation rod portions 30a and 30b may be hinge-coupled to the implant bars 10 and 20.

Accordingly, changes in angles at which the implant bars 10 and 20 are connected to the elongation rod portions 30a and 30b relative to curvatures of the elongation rod portions 30a and 30b may be stably accepted.

Meanwhile, variations in respective curvatures of the first elongation rod portion 30a and the second elongation rod portion 30b, which are reduced at the first temperature or higher, are preferably set to be different from each other to correspond to a direction in which the long bone is curved.

That is, when curvatures of the first elongation rod portion 30a and the second elongation rod portion 30b, which are reduced at the first temperature or higher, have a first variation and a second variation, respectively, one of the first variation and the second variation may be set to be greater than the other thereof. Here, when a variation is set to be great, it is preferably understood that a variation in distance between the end portions is great at the first temperature or higher.

In this case, the variation in the curvature of each of the elongation rod portions(30a and 30b) is preferably set to correspond to the direction in which the long bone is curved. That is, when the long bone 1 is curved toward one end portion of each of the implant bars 10 and 20, the first variation of the first elongation rod portion 30a may be set to be larger than the second variation. Also, when the long bone is curved toward another end portion of each of the implant bars 10 and 20, the second variation of the second elongation rod portion 30b may be set to be higher than the first variation.

Accordingly, a more active growth promotion effect may be given to the growth plate corresponding to the direction in which the long bone is curved than to the growth plate corresponding to a direction opposite to the direction in which the long bone is curved. Thus, the curved long bone may be corrected.

In this case, the end portions of each of the elongation rod portions 30a and 30b are preferably hinge-coupled to the end portions of each of the elongation rod portions 30a and 30b so that the end portions of each of the elongation rod portions 30a and 30b may rotate in a lateral direction.

Figure 4:
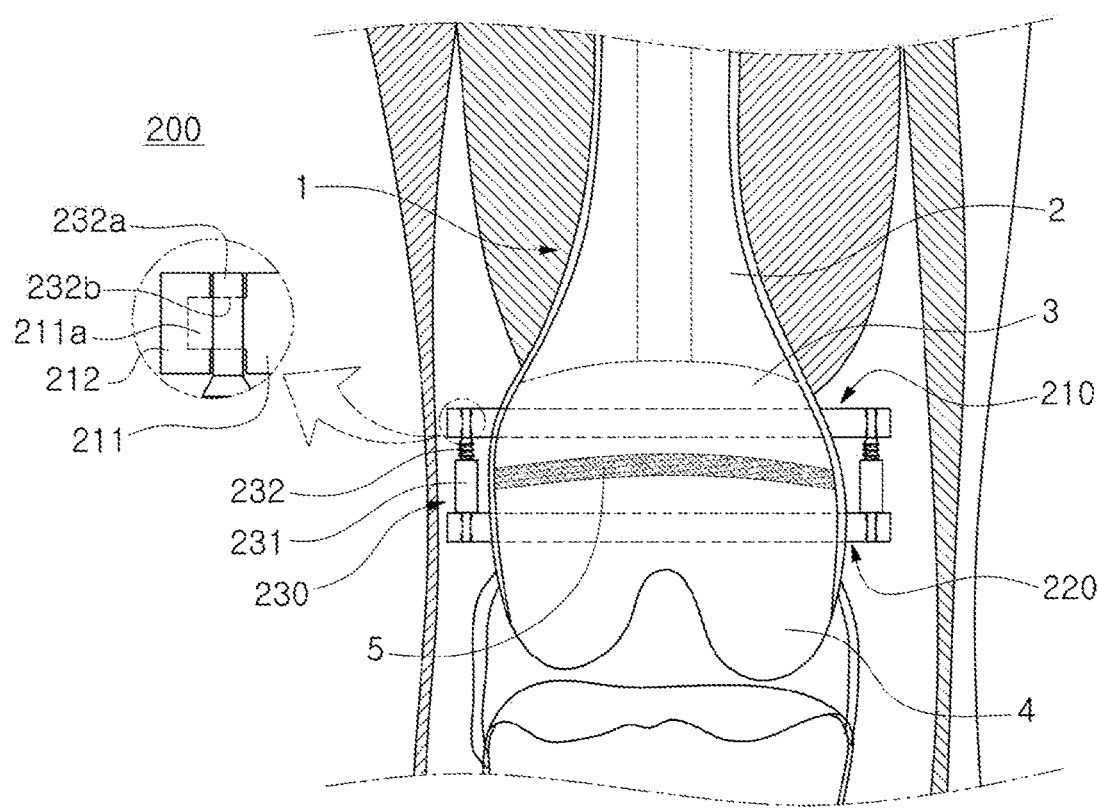
FIG. 4 is a front view of an implant device for promoting bone growth according to a second embodiment of the present disclosure.
Figure 5:
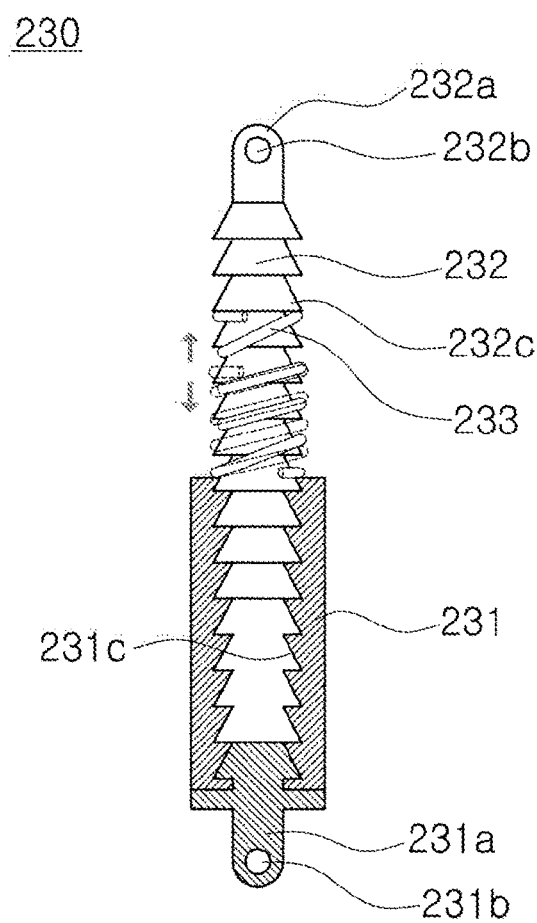
FIG. 5 is a cross-sectional view of a stimulation elongation unit of the implant device for promoting bone growth according to the second embodiment of the present disclosure.

FIG. 4 is a front view of an implant device for promoting bone growth according to a second embodiment of the present disclosure. FIG. 5 is a cross-sectional view of a stimulation elongation unit of the implant device for promoting bone growth according to the second embodiment of the present disclosure. In the present second embodiment, since basic components except for a stimulation elongation unit 230 are the same as in the above-described first embodiment, detailed descriptions of the same components will be omitted.

As can be seen from FIGS. 4 and 5, the stimulation elongation unit 230 preferably includes an inner rod 232, an outer rod 231, and an elastic member 233.

Here, the inner rod 232 is coupled to an end portion of a first implant bar 210, while the outer rod 231 is coupled to an end portion of a second implant bar 220. In this case, the outer rod 231 may be provided as a hollow type, and the inner rod 232 may be inserted into the outer rod 231.

In addition, the elastic member 233 elastically supports between the outer rod 231 and the inner rod 232 so that the inner rod 232 may be withdrawn from the outer rod 231.

Thus, the stimulation elongation unit 230 may be elongated due to elastic force of the elastic member 233, and stimulation for promoting growth may be given to the growth plate 5.

In addition, a serrated protrusion 232c having an inclined upper portion may protrude from an outer circumference of the inner rod 232, while a serrated groove 231c having an inclined upper portion may be formed at an inner circumference of the outer rod 231 to correspond to the serrated protrusion 232c.

Thus, the inner rod 232 may be slidably withdrawn from a lower portion of the outer rod 231 toward an upper portion thereof in an inclined direction of the serrated protrusion 232c.

When the inner rod 232 is withdrawn from the outer rod 231 due to elastic force of the elastic member 233 as described above, a distance between the implant bars 210 and 220 may increase. In this case, a sliding direction of the inner rod 232 is limited to one direction, so that a reduction of the distance between the implant bars 210 and 220 due to external force may be prevented.

That is, with the elongation of the stimulation elongation unit 230, the increased distance between the metaphysis 3 and the epiphysis 4 may be stably maintained, and compressive force for inhibiting growth may be prevented from being applied to the growth plate 5.

Here, an upper hinge portion 232a is formed at an upper end portion of the inner rod 232 and hinge-coupled to a narrow tubular portion 211a formed at the end portion of the first implant bar 210 so that the inner rod 232 may be coupled to the end portion of the first implant bar 210.

Specifically, the first implant bar 210 includes a base bar 211 having the narrow tubular portions 211a provided at both end portions thereof, and fastening portions 212 coupled to end portions of the narrow tubular portions 211a. Also, the fastening portions 212 are coupled to the end portions of the narrow tubular portions 211a that have penetrated binding holes 232b of the upper hinge portion 232a, so that the inner rod 232 may be hinge-coupled to the end portion of the first implant bar 210.

In addition, a lower hinge portion 231a is formed at a lower end portion of the outer rod 231 and hinge-coupled to a narrow tubular portion formed at the end portion of the second implant bar 220 so that the outer rod 231 may be coupled to the end portion of the second implant bar 220.

In this case, the lower hinge portion 231a may be coupled to the narrow tubular portion of the second implant bar 220 through a binding hole 231b formed in the lower hinge portion 231a.

Also, the outer rod 231 may be provided as a hollow type, and the inner rod 232 may be inserted into the outer rod 231.

Here, the outer rod 231 has a lower opening, and the inner rod 232 may be inserted into the outer rod 231 through the lower opening of the outer rod 231 and withdrawn from an upper portion of the outer rod 231. In this case, the lower hinge portion 231a is detachably attached to the outer rod 231. A serrated protrusion having the same shape as that of the inner rod 232 may be formed on the lower hinge portion 231a and fastened to the lower opening of the outer rod 231.

A communication hole is preferably formed in the lower hinge portion 231a so that an inner pressure of a hollow of the outer rod 231 may not be reduced when the inner rod 232 is withdrawn.

In addition, the outer rod 231 and the inner rod 232 preferably include an alloy or a synthetic resin material, which has predetermined elastic force without causing a negative reaction to the human body.

Meanwhile, the serrated protrusion 232c and the serrated groove 231c are formed in multiple stages along a lengthwise direction of each of the outer rod 231 and the inner rod 232. Preferably, the elastic member 233 includes a coil spring including a shape memory alloy material, which is elongated at a predetermined first temperature or higher and contracted at a predetermined second temperature or lower, and is mounted on an outer circumference of the inner rod 232.

Here, the elastic member 233 preferably includes a two-way shape memory alloy configured to memorize both an Austenite-phase shape and a Martensite-phase shape so that a shape of the two-way shape memory alloy may be shifted by heating and cooling processes.

In this case, the first temperature is preferably set to about 36.5° C., which is similar to body temperature, and the second temperature is preferably set to a temperature lower than the first temperature, which is not naturally generated in the body.

In addition, when the elastic member 233 is elongated and contracted, a length difference of the elastic member 233 may be set to a minute value corresponding to a height of one or two serrated protrusions 232c.

Specifically, the elastic member 233 is mounted such that a lower end portion of the elastic member 233 is seated on an upper end of the outer rod 231, while an upper end portion of the elastic member 233 is engaged with the lower portion of the serrated protrusion 232c of the inner rod 232.

In this case, the elastic member 233 is installed while being cooled and contracted, and heated by body temperature and elongated. Also, in a state in which the elongated lower end portion of the elastic member 233 is seated on the upper end of the outer rod 231, a flat engaging surface formed in the lower portion of the serrated protrusion (232c) is applied with pressure upward by the upper end portion of the elastic member 233. Accordingly, the inner rod 232 may be withdrawn from the outer rod 231.

Thus, the stimulation elongation unit 230 may be elongated, and a distance between the implant bars 210 and 220 may be increased.

As described above, the implant bars 210 and 220 are spaced apart from each other by a distance corresponding to a height of one serrated protrusion 232c during the elongation of the elastic member 233 so as not to apply excessive stimulation to the growth plate 5. Thus, the growth plate 5 may be safely stimulated.

In addition, when the elongation of the stimulation elongation unit 230 is completed, the elastic member 233 is cooled by applying a cold pack or the like on skin tissues.

In this case, in a state in which the lower end portion of the elastic member 233 is engaged with an engaging surface of a lower portion of the serrated protrusion 232c, the upper end portion of the elastic member 233 may slide down and contracted along an inclined surface of an upper portion of the serrated protrusion 232c.

In addition, the contracted elastic member 233 may be reheated by body temperature at the time of the removal of a cold pack or the like and elongated in the same process between the lower engaging surface of the serrated protrusion 232c and the upper end of the outer rod 231.

As described above, as the elastic member 233 is cooled and heated, a process of sliding the upper end portion of the elastic member 233 down along the inclined surface of the upper portion of the serrated protrusion 232c and elastically applying pressure to the engaging surface of the lower portion of the serrated protrusion 232c may be repeated.

Thus, the stimulation elongation unit 230 may be continuously elongated such that a certain amount of stimulation may be repetitively applied to the growth plate 5. Furthermore, in the related art, it was possible to promote growth of about 1 cm to about 2 cm by using a once installed device. In another case, when the implant device 100 for promoting bone growth is installed once, the long-growth promoting implant device 100 may be used over a long period of time until the growth of the long bone 1 is completed in a wide range corresponding to an overlapping length between the inner rod 232 and the outer rod 231. Thus, efficiency of a product may be improved.

Meanwhile, stimulation elongation units 230 may be respectively located between one end portions of the implant bars 210 and 220 and between another end portions of the implant bars 210 and 220. The respective stimulation elongation units 230 may include elastic members having different variations.

Thus, one stimulation elongation unit and another stimulation elongation unit may be set to have different elongated lengths.

In this case, a variation of each of the elastic members may be set to correspond to a direction in which the long bone is curved. A variation of the elastic member located on a curved side of the long bone may be set to be larger than variations of elastic members located on other sides so that the curved long bone may be corrected.

Furthermore, end portions of each of the stimulation elongation units is preferably hinge-coupled to end portions of each of the implant bars so that the end portions of each of the stimulation elongation units may rotate in a lateral direction.

As described above, the present disclosure is not limited to each of the above-described embodiments, and it will be understood that the embodiments may be modified by one of ordinary skill in the art to which the present disclosure belongs, without departing from the spirit and scope of the following claims. The modified embodiments fall within the scope of the present disclosure.

INDUSTRIAL APPLICABILITY

The present disclosure provides an implant device for promoting bone growth and can be applied to the industry of implant devices for promoting bone growth.

The invention claimed is:
1. An implant device for promoting bone growth, the implant device comprising:
a first implant bar configured to be implanted to penetrate a metaphysis corresponding to inside of a growth plate of a long bone to be treated;
a second implant bar configured to be implanted to penetrate an epiphysis of outside of the growth plate; and
at least one stimulation elongation unit configured to be located close to an external surface of the long bone to be treated and configured to be provided in skin tissues surrounding the long bone to be treated, the stimulation elongation unit elongated between each end portion of the first implant bar and the second implant bar to increase a distance between the first implant bar and the second implant bar to cause the growth plate to be extended,
wherein one of the at least one stimulation elongation unit comprises:
an inner rod coupled to one end portion of the first implant bar;
an outer rod having a hollow coupled to one end portion of the second implant bar, the outer rod into which the inner rod is inserted; and
an elastic member configured to elastically support between the inner rod and the outer rod, and the inner rod is at least partially withdrawn from the outer rod,
wherein the elastic member includes a coil spring, made of a shape memory alloy material, elongated at a predetermined first temperature or higher and contracted at a predetermined second temperature or lower,
wherein the elastic member is mounted on the outer circumference of the inner rod, and
wherein the elastic member elastically applies pressure to an engaging surface of a lower portion of each of a plurality of serrated protrusions when the elastic member is elongated, and is slid along the inclined upper portion of each of the plurality of the serrated protrusions when the elastic member is contracted.
2. The implant device of claim 1, wherein the end portion of the first implant bar and the end portion of the second implant bar are configured to be exposed to one-side portion of the long bone, and another end portion of the first implant bar and another end portion of the second implant bar are configured to be exposed to another-side portion of the long bone.
3. The implant device of claim 1, wherein the at least one stimulation elongation unit comprises a first stimulation elongation unit and a second stimulation elongation unit,
wherein the first stimulation elongation unit is located between the end portion of the first implant bar and the end portion of the second implant bar, and
wherein the second stimulation elongation unit is located between another end portion of the first implant bar and another end portion of the second implant bar.
4. The implant device of claim 1, wherein each of the plurality of serrated protrusions comprises an inclined upper portion to protrude from an outer circumference of the inner rod, and each of a plurality of serrated grooves comprises an inclined upper portion at an inner circumference of the outer rod, wherein the inner rod is slid in a longitudinal direction of the outer rod.

* * * * *